(12) United States Patent
Trivedi et al.

(10) Patent No.: US 8,927,227 B2
(45) Date of Patent: Jan. 6, 2015

(54) METHOD OF MEASURING EFFECTS OF COMPONENTS ON CELL REACTIVE OXYGEN SPECIES PRODUCTION

(75) Inventors: Harsh M. Trivedi, Somerset, NJ (US); Dandan Chen, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 429 days.

(21) Appl. No.: 12/991,539

(22) PCT Filed: May 6, 2009

(86) PCT No.: PCT/US2009/042958
§ 371 (c)(1),
(2), (4) Date: Nov. 8, 2010

(87) PCT Pub. No.: WO2009/137560
PCT Pub. Date: Nov. 12, 2009

(65) Prior Publication Data
US 2011/0065144 A1    Mar. 17, 2011

Related U.S. Application Data

(60) Provisional application No. 61/050,871, filed on May 6, 2008.

(51) Int. Cl.
*C12Q 1/02* (2006.01)
*G01N 33/50* (2006.01)

(52) U.S. Cl.
CPC .............. *C12Q 1/02* (2013.01); *G01N 33/5038* (2013.01)
USPC ........................................................ 435/29

(58) Field of Classification Search
None
See application file for complete search history.

(56) References Cited

U.S. PATENT DOCUMENTS

| | | | |
|---|---|---|---|
| 7,087,766 B2 | 8/2006 | Nagano et al. | |
| 7,378,282 B2 | 5/2008 | Setsukinai et al. | |
| 2003/0022818 A1 | 1/2003 | Miller et al. | |
| 2006/0289313 A1 | 12/2006 | Yuasa et al. | |
| 2009/0017057 A1* | 1/2009 | Chen et al. | 424/193.1 |
| 2010/0004210 A1* | 1/2010 | Roecken et al. | 514/110 |

FOREIGN PATENT DOCUMENTS

| | | |
|---|---|---|
| EP | 1328245 | 7/2003 |
| JP | 2003-189893 A | 7/2003 |
| JP | 2004-233164 A | 8/2004 |
| JP | 2005-047898 A | 2/2005 |
| JP | 2005-095171 A | 4/2005 |
| JP | 2007-077065 A | 3/2007 |
| JP | 2007-138961 A1 | 12/2007 |
| WO | WO 98/02727 | 1/1998 |
| WO | WO 2007/130589 | 11/2007 |

OTHER PUBLICATIONS

Chen et al., 2008, "Real-time Monitoring of Intracellular ROS and Screening of Antioxidant Additives", IADR Annual Meeting, Abstract #:1283.
Chemyak et al., 2006, "Production of Reactive Oxygen Species in Mitochondria of HeLa Cells under Oxidative Stress", Biochimica et Biophysica Acta, 1757(5-6):525-534.
Datta et al, 2000, "Reactive Oxygen Species in Health and Disease", The National Medical Journal of India, 13(6)304-310.
Kweon, et al., 2001, "Real-time Measurement of Intracellular Reactive Oxygen Species using Mito tracker Orange ($CMH_2TMRos$)", Bioscience Reports 21(3):341-352.
Tada et al., 2004, "Nitric Oxide and Reactive Oxygen Species Do Not Elicit Hypersensitive Cell Death but Induce Apoptosis in the Adjacent Cells During the Defense Response of Oat", Molecular plant-microbe interactions : MPMI, 17(3):245-253.
International Search Report and Written Opinion for International Application No. PCT/US2009/042958 mailed on Jul. 31, 2009.
LeGrand-Poels et al. "Activation of the Transcription Factor NF-kappa-B in Lipopolysaccaride-Stimulated U937 Cells," Biochemical Pharmacology, vol. 53, No. 3, 1997, pp. 339-346.
Zurgil et al. "Concomitant Real-Time Monitoring of Intracellular Reactive Oxygen Species and Mitochondrial Membrane Potnetial in Infividual Living Promonocytic Cells," Journal of Immunological Methods, vol. 316, No. 1-2, Oct. 30, 2006, pp. 27-41.
Greengard, 2001, "The Neurobiology of Dopamine Signaling," Bioscience Reports 21(3):341-3352.

* cited by examiner

*Primary Examiner* — Lisa J Hobbs
(74) *Attorney, Agent, or Firm* — Anne Louise St. Martin

(57) ABSTRACT

A method of determining the effects of a test component on intracellular ROS levels. The method can be used in marketing or in screening for useful components in reducing ROS levels in cells adversely affected by increased ROS generation.

7 Claims, 2 Drawing Sheets

METHOD OF MEASURING EFFECTS OF COMPONENTS ON CELL REACTIVE OXYGEN SPECIES PRODUCTION

CROSS-REFERENCE TO RELATED PATENT APPLICATIONS

The present application is a national stage entry under 35 U.S.C. §371 of International Patent Application No. PCT/US2009/042958, filed May 6, 2009, which in turn claims the benefit of U.S. Provisional Patent Application No. 61/050,871, filed May 6, 2008, the entireties of which are hereby incorporated by reference.

BACKGROUND OF THE INVENTION

Reactive oxygen species (ROS) are cellular byproducts formed by the metabolism of oxygen, are responsible for cell oxidative damages, and can be the cause of cellular injury, cellular dysfunction, and cell death (apoptosis). The effects of ROS on cell metabolism have been well documented. Accumulation of ROS in tissue may cause oxidative injury, and thus it may be desirable to reduce the amounts of ROS in tissues. It is desirable to monitor ROS generation in cells to determine whether ROS are involved in diseases including cardiovascular, inflammatory, and infectious diseases. Cells normally are capable of preventing oxidative damage from ROS with enzymes, such as superoxide dismutase or catalase. Other compounds also are useful in preventing such damage, including antioxidants such as vitamins, uric acid, and glutathione. Such compounds, (e.g., antioxidants), may play an important role in scavenging free radicals and protecting the host organism from pathogens.

Although many methods have been developed to measure ROS quantities in tissue, there are few methods that measure intracellular ROS concentrations in real time. The ability to measure ROS quantities is important, in that ROS concentrations may change, e.g., increase or decrease, over time.

Accordingly, there is a continuing interest in developing and administering effective antioxidant compositions to prevent ROS damage. There are few methods, however, that are capable of measuring the effects of compositions on ROS production in real time. It therefore would be desirable to develop methods that can measure the effects of components on intracellular ROS production.

BRIEF SUMMARY OF THE INVENTION

In accordance with certain embodiments, a method is provided that can be utilized to measure intracellular ROS concentrations in real time. The method of the embodiments may be useful in determining the effects of test components on intracellular ROS production and oxidative stress on a cell. The methods also may be useful to determine the ability of test components to reduce ROS components in a cell, in which the ROS which may be endogenous or exogenous to the cell.

Thus, certain embodiments described herein include a method of measuring the effect a test component has on the production of ROS in a cell. The method includes contacting a cell with a material capable of fluorescence, contacting the cell with a test component, contacting the cell with an ROS or an ROS stimulant, and measuring cell fluorescence. The embodiments further include measuring cell fluorescence after contacting the cell with the material capable of fluorescence and either an ROS or an ROS stimulant, measuring cell fluorescence after contacting the cell with a test component, comparing the two fluorescence values and determining whether the test component reduced ROS.

DETAILED DESCRIPTION OF THE INVENTION

Figure 1:
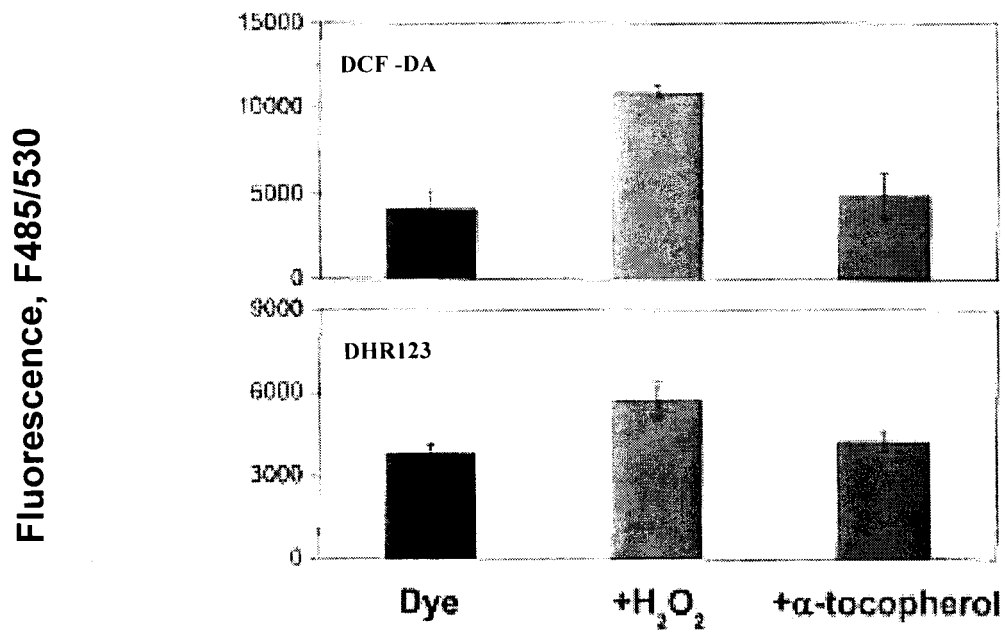
FIG. 1 shows the fluorescence values obtained when U937 cells are: stained only with dye (DCF-DA and DHR123), incubated in the presence of $H_2O_2$; incubated in the presence of α-tocopherol.

As used throughout this description, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Throughout this description, use of articles "the," "a," "an," or the like is not intended to limit the embodiments to a singular form of the item. For example, the expression "a component" can denote a single component or multiple components. Component in the embodiments includes chemical compounds, small and large peptides and proteins, DNA that express small and large peptides and proteins, and the like.

The method includes contacting a cell with a material capable of fluorescence when oxidized or reduced, contacting the cell with a test component, contacting the cell with an ROS or an ROS stimulant, and measuring cell fluorescence. Preferably, the material capable of fluorescence is a dye that fluoresces when oxidized, more preferably a dye selected from 2,7-dichlorofluorescein diacetate (DCF-DA), dihydrorhodamine (DHR 123), and mixtures thereof. The method also includes use of a material that is capable of fluorescence when reduced.

A preferred method includes the use of an antioxidant as the test compound. Another preferred method includes as the ROS an oxygen ion generating compound, free radical generating compound, a peroxide, or combinations thereof. Preferably the ROS is a peroxide, and more preferably hydrogen peroxide. Other preferred methods include the use of an ROS stimulant, such as an inflammatory mediator.

The method of the preferred embodiments also includes as the ROS stimulant: (i) a bacterial endotoxin, exotoxin, or combinations thereof; or (ii) a lipopolysaccharide, lipooligosaccharide, or combinations thereof. Preferably, the ROS is a lipopolysaccharide.

A cell useful with various methods of preferred embodiments include an immune cell, a lymphocyte, lymphoblast, macrophage, a nucleated cell such as mitochondria, or mixtures thereof. The cell may be immortalized, or present in a tissue culture. Preferably, the cell has a cell wall that is permeable by a dye. In addition, the dye may accumulate in the cell mitochondria. It is preferred that any excess dye is washed from the cell.

In the method of the preferred embodiments, the test compound is transported into the cell, either actively or passively.

Preferably, any excess test compound is washed from the cell. In a similar vein, the ROS or ROS stimulant (e.g., inflammatory mediator) preferably is transported into the cell, either actively or passively, and it is preferred to wash any excess ROS or ROS stimulant from the cell.

In accordance with various aspects of preferred embodiments, a cell initially is contacted with a material capable of fluorescence when oxidized or reduced, preferably a dye. Dyes useful in the present embodiments include dyes that fluoresce when oxidized or reduced. Preferably, such dyes fluoresce when oxidized or reduced, e.g., by a ROS. It is preferred to use dyes that are contacted with cells in a non-fluorescent form, and then fluoresce when reacted with a ROS, e.g., ROS either produced intracellularly or introduced from external sources. Some useful dyes that possess these attributes are known to those having ordinary skill in the art, and may include fluorescein type dyes, such as 2,7-dichlorofluorescein diacetate (DCF-DA). DCF-DA is a membrane-permeable dye that may diffuse across the cell lipid membrane. It is non-fluorescent when inactive, and forms a highly fluorescent dichlorofluorescein (DCF) when it is oxidized by ROS. Other dyes useful in the present invention may include fluorescein derivatives and analogs, such as dihydrorhodamine (DHR 123), which is an analog of DCF-DA. DHR123 accumulates in mitochondria, and therefore may be particularly useful in determining ROS levels in the same. Other useful dyes may include derivatives of fluorescein, such as Oregon Green, Tokyo Green, carboxyseminaphthofluorescein (SNAFL—available from Molecular Probes, (Invitrogen Corp.), Carlsbad, Calif.), carboxynaphthofluorescein, Alexa Fluor dyes (e.g., Alexa 488—also available from Molecular Probes, (Invitrogen Corp.), Carlsbad, Calif.), DyLight Fluor dyes (e.g., DyLight 488, commercially available from Thermo Fisher Scientific, Waltham, Mass.), and HiLyte Fluor dyes (commercially available from AnaSpec, San Jose, Calif.). The cells may be incubated with the dye to allow for incorporation of the dye into the cell. Afterwards, the cells may be washed to remove residual dye.

Following labeling with a dye, the cell may be exposed to one or more test compounds. Such test compounds preferably are introduced into the cell by active or passive transport, e.g., diffusion, and are preferably retained within the cell. The cells may be incubated in the presence of such test compounds, and then washed to remove residual test compounds.

Following treatment with the test compound, the cell then preferably is exposed to ROS. ROS typically include oxygen ions, free radicals, and peroxides, both inorganic and organic, and compounds that generate such oxygen ions and free radicals intracellularly. ROS (or ROS agents) are known to those having ordinary skill in the art, and generally are small molecules that are highly reactive due to the presence of unpaired valence shell electrons. Examples of peroxides include hydroperoxides, hydrogen peroxide, peroxides of alkali and alkaline earth metals, organic peroxy compounds, peroxy acids, and mixtures thereof. The cell may be exposed to the ROS agents from an external source, in which the cell may be incubated in media containing the ROS agent to allow for the cell to incorporate the ROS agent intracellularly, e.g., either by active or passive transport. The cells then may be washed to removed residual ROS that has not been incorporated into the cell.

In one embodiment of the present invention, ROS may be contacted with a cell in conjunction with a compound that induces ROS production, e.g., a ROS stimulant, such as an inflammatory mediator in which the mediator causes or is known to cause ROS production in a cell. In yet another embodiment the cell is contacted with the ROS stimulant in the absence of the additional ROS agent. As is known in the art, the inflammatory mediator may include a bacterial toxin, e.g., an endotoxin or exotoxin, such as a lipopolysaccharide or lipooligosaccharide. The cell may be incubated with the ROS and inflammatory mediator so as to allow the ROS and inflammatory mediator to be incorporated into the cell. The cell may then be washed to remove residual ROS and inflammatory mediator. Alternatively, the cell may be incubated with the inflammatory mediator so as to allow the inflammatory mediator to be incorporated into the cell. The cell then may be washed to remove residual inflammatory mediator.

The methods of the embodiments described herein contemplate measuring fluorescence of the cells that have been contacted with the various components. The methods include measuring fluorescence after contacting the cells with the material capable of fluorescence and the ROS or ROS stimulant, and then measuring fluorescences after contacting the cells with these components and the test compound. Fluorescence may be determined by any method known by those having ordinary skill in the art and readily available. Such known and commercially available methods include optical live cell array technology or microscope imaging systems. As is well known, fluorescence typically is measured at excitation and at emission. Persons having ordinary skill in the art are capable of measuring and determining fluorescence, using the guidelines provided herein.

Without intending to be bound by any theory, it is believed that the methods of the present invention allows for real-time analysis of the effects of test compounds on intracellular ROS levels. By incorporating a component capable of fluorescence, a test compound, and then a ROS/inflammatory mediator into the cells, one is able to measure the antioxidant activity of the test compound by measuring cell fluorescence. The component capable of fluorescence upon oxidation or reduction, preferably a dye, typically has some background fluorescence, but upon binding to free radicals, the fluorescence intensity increases. That increase in fluorescence intensity can readily be measured. Test compounds can be added to the cells to assess their ability to reduce the formation of ROS free radicals (or consume them by reaction), and if capable of reducing free radical formation, the fluorescence intensity should decrease.

Accordingly, a test compound that has a greater ability to inhibit ROS results in a reaction in which less ROS is able to react with the dye, and thus there is reduced fluorescence. On the other hand, a test compound that does not inhibit ROS results in a reaction in which a greater amount of ROS is able to react with the dye, and thus there is increased fluorescence. Cellular fluorescence may be monitored over a period of minutes, hours, or days to determine the effect of the test compound on the ROS/inflammatory mediator.

In one embodiment, the cell is contacted with a dye before being contacted with a test compound. Optionally, the cell is contacted with a test compound before being contacted with a ROS and/or ROS stimulant. In another embodiment, the ROS is introduced into the cell, e.g., the ROS is exogenous to the cell.

Cells useful in the preferred methods include nucleated cells having mitochondria. The cells may be immortalized, e.g., cancer cells, and may be immune cells, such as a lymphocyte, or lymphoblast cells. Such cells may be cultured in any number of methods known by those of skill in the art. The cells also may be cultured on-site during an operative or examination procedure, and then tested in real time to assess the effects of certain test compounds on inhibiting cellular production of ROS.

The methods of the embodiments are useful in determining the effects compounds have on the production of ROS in cells. As stated above, it is known that the generation of free radicals in a cell is undesirable, often resulting in cell death. For example, certain bacteria have the effect of inducing free radical formation in human cells and consequently, damage the cells. The methods described herein are capable of determining test compounds that can reduce free radical formation (resulting in lower fluorescent intensity), and thus may be useful in counter-acting the deleterious effects of the bacteria.

Many such bacteria exist in the oral cavity and oral mucosa. The bacteria may cause any number of deleterious effects. For example, bacterial cells may be used as the cells of the preferred embodiments, preferably, facultative anaerobe cells. The method then can measure the ability of certain test compounds to reduce the free radical generation of such cells.

The methods of the embodiments therefore can be used on-site to determine an effective therapy (administration of an efficacious test compound that adequately reduced fluorescence) for treating certain cells susceptible to free radical generation. The methods of the embodiments also are useful in demonstrating the efficacy of certain compounds (or compositions containing these compounds) on known cells, e.g., bacterial cells. For example, the method can be used to show a dental professional how effective a certain dentifrice is in reducing free radical generation in bacteria cells commonly found in the human mouth. The method also can be used as a comparative tool in marketing a product by showing comparisons between products (e.g., dentifrices of various competitors).

The preferred embodiments of invention now will be described with respect to the following non-limiting example. The example is merely illustrative and does not in any way limit the scope of the invention as described and claimed.

EXAMPLE 1

Human histocytic lymphoma U937 cells (ATCC, Manassas, Va.) were initially cultured in RPMI-1640 media (ATCC, Manassas, Va.) containing 10% serum and 1% penicillin, and then transferred at a concentration of $2 \times 10^5$ cells/ml into media containing 1 ng/ml PMA for 48 hours at 37° C. The cells were starved overnight in serum-free culture media before exposure to dye.

Cells were washed with PBS buffer twice, and divided into two sets to be incubated with DCF-DA or DHR123 (Calibochem, La Jolla, Calif.) for 30 minutes at 30° C. Cells are washed with PBS twice to remove residual dye. Appropriate experimental controls are also maintained.

Cells are then divided into several groups, and various amounts of a 1% solution of α-tocopherol (Vitamin E), substance 1, or substance 2 is added to each of the groups, and incubated at 37° C. for 15 minutes. Cells then were washed twice with PBS to remove residual amounts of test compounds. ROS agents $H_2O_2$ and LPS then were added and incubated for different periods of time. Fluorescence of the cells then were read at excitation 485 nm and emission 530 nm for up to 5 hours.

Figure 2:
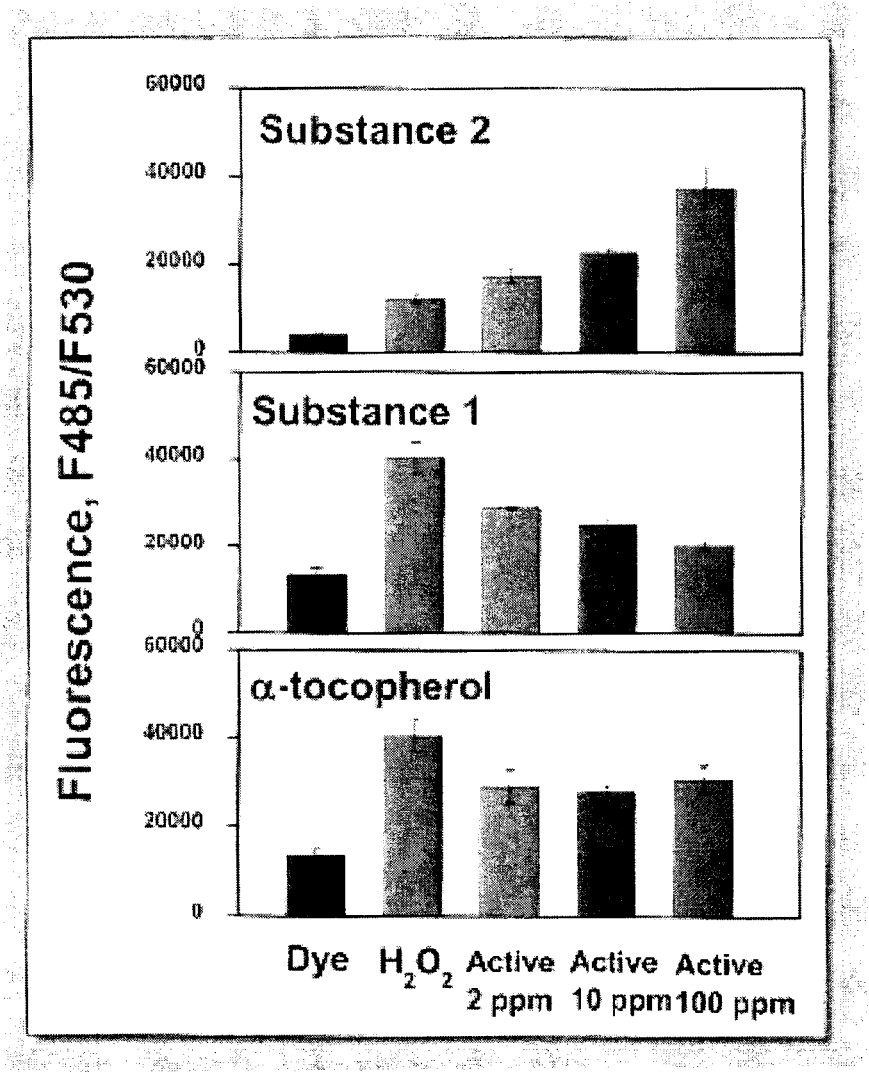
FIG. 2 shows the fluorescence values obtained when U937 cells are: stained only with dye (DCF-DA and DHR123), incubated in the presence of $H_2O_2$; incubated in the presence of an active at 2 ppm, 10 ppm or 100 ppm, wherein the active is α-tocopherol, substance 1 or substance 2.

As shown in FIGS. 1 and 2, cells stained only with dye, e.g., DCF-DA and DHR123 exhibit background fluorescence. Referring to FIG. 1, following two hours of incubation, cells incubated in the absence of a test compound but in the presence of the ROS at 2.5 mM and ROS stimulant fluoresce greater than cells incubated in the presence of a test compound (α-tocopherol) and ROS at 2.5 mM and ROS stimulant.

Analysis of cell fluorescence therefore allows real-time monitoring of intracellular oxidative stress that can be used to screen test compounds. Measurement of cell fluorescence may be accomplished with optical live cell array technology, and/or microscope imaging systems in individual cells.

Referring to FIG. 2, 2 ppm, 10 ppm, or 100 ppm of α-tocopherol, substance 1, and substance 2 were incubated with the cells. FIG. 2 reveals that in the presence of 2.5 mM of hydrogen peroxide, 2 ppm of α-tocopherol and substance 1 reacted with ROS and reduced the oxidative level by approximately 30%. At 10 ppm and 100 ppm, α-tocopherol did not show enhanced capability in scavenging ROS or free radicals; however, 100 ppm of substance 1 reduced the oxidative level by 50%. FIG. 2 also reveals that substance 2 enhanced the oxidative level, and that substance 2 increased to nearly 3 times the free radical level at 100 ppm, when compared to 2 ppm.

It will be appreciated by those having ordinary skill in the art that changes and alterations may be made to the embodiments described above without departing from the broad inventive concept thereof. It is understood, therefore, that this invention is not limited to the particular embodiments disclosed, but it is intended to cover modifications within the spirit and scope of the present invention.

We claim:

1. A method of measuring the efficacy of an antioxidant in reducing ROS (reactive oxygen species) components in a cell selected from the group consisting of lymphocyte, lymphoblast, macrophage, bacteria, facultative anaerobe, and mixtures thereof comprising:
   a. contacting a cell with a dye that fluoresces when oxidized or reduced;
   b. contacting the cell with the antioxidant, wherein the antioxidant is transported into the cell;
   c. measuring cell fluorescence;
   d. contacting the cell with an ROS and a ROS stimulant wherein the ROS is selected from the group consisting of an oxygen ion generating compound, free radical generating compound, a peroxide, and mixtures thereof, and wherein the ROS stimulant is selected from the group consisting of bacterial exotoxin, lipopolysaccharide and mixtures thereof; and
   e. measuring cell fluorescence; and
   f. comparing the cell fluorescence from c with the fluorescence from e and determining the efficacy of the antioxidant in reducing ROS.

2. The method of claim 1, wherein the dye is selected from the group consisting of 2,7-dichlorofluorescein diacetate (DCF-DA), dihydrorhodamine (DHR123), and mixtures thereof.

3. The method of claim 1, wherein the ROS is a peroxide.

4. The method of claim 3, wherein the peroxide is hydrogen peroxide and the ROS stimulant is a lipopolysaccharide.

5. The method of claim 1, wherein the cell has a wall that is permeable by the material capable of fluorescence.

6. The method of claim 1, wherein the antioxidant is actively or passively transported into the cell.

7. The method of 1, wherein the ROS is transported into the cell by active or passive transport.

* * * * *